(12) United States Patent
Sharonov (10) Patent No.: US 9,492,069 B2
(45) Date of Patent: Nov. 15, 2016

(54) SURGICAL CAMERA ASSEMBLIES AND SYSTEMS

(71) Applicant: COVIDIEN LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 623 days.

(21) Appl. No.: 13/913,547

(22) Filed: Jun. 10, 2013

(65) Prior Publication Data
US 2014/0012139 A1 Jan. 9, 2014

Related U.S. Application Data

(60) Provisional application No. 61/667,607, filed on Jul. 3, 2012, provisional application No. 61/712,895, filed on Oct. 12, 2012.

(51) Int. Cl.
| | |
|---|---|
| *A61B 1/313* | (2006.01) |
| *A61B 1/05* | (2006.01) |
| *A61B 1/00* | (2006.01) |
| *A61B 5/00* | (2006.01) |
| *A61B 17/00* | (2006.01) |

(52) U.S. Cl.
CPC ......... *A61B 1/3132* (2013.01); *A61B 1/00124* (2013.01); *A61B 1/05* (2013.01); *A61B 90/361* (2016.02); *A61B 5/0084* (2013.01); *A61B 90/30* (2016.02); *A61B 90/37* (2016.02); *A61B 90/50* (2016.02); *A61B 2017/00477* (2013.01); *A61B 2017/00734* (2013.01); *A61B 2090/309* (2016.02); *A61B 2090/3616* (2016.02)

(58) Field of Classification Search
CPC .. A61B 1/3132; A61B 1/05; A61B 1/00066; A61B 1/00124; A61B 19/5212
See application file for complete search history.

(56) References Cited

U.S. PATENT DOCUMENTS

| | | | | |
|---|---|---|---|---|
| 4,941,456 A * | 7/1990 | Wood | ................. | G02B 23/2476 348/69 |
| 5,159,446 A * | 10/1992 | Hibino | ............... | A61B 1/00039 348/65 |
| 6,224,542 B1 * | 5/2001 | Chang | ................ | A61B 1/00039 600/109 |
| 6,293,910 B1 * | 9/2001 | Yamakita | ............. | A61B 1/0011 600/110 |
| 6,387,043 B1 * | 5/2002 | Yoon | ................... | A61B 1/00052 600/104 |
| 2006/0074307 A1 * | 4/2006 | Igarashi | ............. | A61B 1/00039 600/434 |
| 2007/0225573 A1 * | 9/2007 | Stokes | ................ | A61B 1/3132 600/249 |

(Continued)

FOREIGN PATENT DOCUMENTS

EP 2371264 A1 10/2011

OTHER PUBLICATIONS

European Search Report 13174622 dated Oct. 1, 2013.

(Continued)

*Primary Examiner* — John P Leubecker (57) ABSTRACT

A surgical camera assembly includes a camera member and a receptacle member. The camera member includes a camera head and a shaft. The shaft includes at least one electrical contact positioned towards a free end thereof. The at least one electrical contact is electrically coupled to the camera head. The receptacle member is configured to releasably receive the free end of the shaft and includes at least one electrical contact that is configured to electrically couple to the at least one electrical contact of the shaft to establish electrical communication between the camera head and the receptacle member when the free end of the shaft is received within the receptacle member.

15 Claims, 6 Drawing Sheets

(56) References Cited

U.S. PATENT DOCUMENTS

| | | | | |
|---|---|---|---|---|
| 2007/0232863 | A1* | 10/2007 | Miyake | A61B 1/00045 600/204 |
| 2008/0309758 | A1 | 12/2008 | Karasawa et al. | |
| 2008/0312499 | A1* | 12/2008 | Handa | A61B 1/0005 600/109 |
| 2010/0036199 | A1* | 2/2010 | Karasawa | A61B 1/00085 600/109 |
| 2010/0076259 | A1* | 3/2010 | Asada | A61B 1/00096 600/102 |
| 2011/0046440 | A1* | 2/2011 | Asada | A61B 1/00147 600/104 |
| 2011/0257488 | A1* | 10/2011 | Koyama | A61B 1/00147 600/249 |
| 2012/0296163 | A1* | 11/2012 | Stopek | A61B 19/5212 600/109 |
| 2012/0310045 | A1* | 12/2012 | Hu | A61B 1/00018 600/110 |
| 2014/0066711 | A1* | 3/2014 | Farin | A61B 1/0676 600/109 |

OTHER PUBLICATIONS

Chinese Office Action issued in corresponding application No. 2013102772878 on Jun. 1, 2016.

* cited by examiner

SURGICAL CAMERA ASSEMBLIES AND SYSTEMS

CROSS REFERENCE TO RELATED APPLICATIONS

The present application claims the benefit of and priority to U.S. Provisional Patent Application Ser. No. 61/667,607, filed Jul. 3, 2012. The present application also claims the benefit of and priority to U.S. Provisional Patent Application Ser. No. 61/712,895, filed Oct. 12, 2012, which is expressly incorporated herein by reference in its entirety.

BACKGROUND

1. Technical Field

The present disclosure relates to surgical instruments and, more particularly, to surgical camera assemblies and systems that facilitate visualization of an internal surgical site.

2. Background of Related Art

Endoscopic surgical procedures are minimally-invasive procedures in which operations are carried out within the body by using elongated instrumentation inserted through small entrance openings in the body. Minimally-invasive procedures are desirable in that they allow for quicker recovery time and shorter hospital stays as compared to open surgical procedures. Minimally-invasive procedures also leave minimal scarring (both internally and externally) and reduce patient discomfort during the recovery period. However, because the interior dimensions of the entrance openings into the body are necessarily small, only elongated, small diametered instrumentation may be used to access the internal surgical site.

During a typical minimally-invasive surgical procedure, one or more surgical cameras and/or illumination sources, e.g., one or more endoscopes, are inserted through an access portal disposed within an opening in the body and into the internal surgical site to permit the user to visualize the internal surgical site. The surgical instrumentation used to carry out the procedure to be performed is likewise inserted through the access portal and into the internal surgical site. However, in some instances, it is desirable to space-apart the surgical camera(s) from one another, the surgical instrumentation used to perform the procedure, and/or the illumination source(s), thus necessitating the use of two or more access openings. Further, where panoramic, three-dimensional, multi-angle, or multi-camera visualization of the internal surgical site is desired, multiple surgical cameras and illumination sources are inserted into the internal surgical site through the same or additional access portals. Those inserted through the same access portal take up valuable space within the access portal, necessitating a greater amount of insertion/removal/replacement of instrumentation during the procedure, while multiple access openings are required to accommodate the separate or spaced-apart insertion of the surgical cameras and illumination sources.

SUMMARY

In accordance with the present disclosure, a surgical camera assembly is provided including a camera member and a receptacle member. The camera member includes a camera head and a shaft. The shaft includes at least one electrical contact positioned towards a free end thereof. The at least one electrical contact is electrically coupled to the camera head. The receptacle member is configured to releasably receive the free end of the shaft of the camera member. The receptacle member includes at least one electrical contact that is configured to electrically couple to the at least one electrical contact of the shaft to establish electrical communication between the camera head and the receptacle member when the free end of the shaft is received within the receptacle member.

In embodiments, the free end of the shaft defines a needle-shaped configuration to facilitate penetration through tissue.

In embodiments, the receptacle member defines a receiving port configured to receive the free end of the shaft. Further, the at least one electrical contact of the shaft may be disposed about an outer periphery of the shaft and the at least one electrical contact of the receptacle member may be disposed within the receiving port such that electrical communication is established between the camera head and the receptacle member when the free end of the shaft is received within the receiving port.

In embodiments, the free end of the shaft is configured for releasable friction-fit engagement within the receiving port of the receptacle member.

In embodiments, the receptacle member includes control circuitry disposed therein. The control circuitry is coupled to at least one of the electrical contacts of the receptacle member and is configured to transmit control signals to the camera head when the camera head and the receptacle member are disposed in electrical communication with one another.

In embodiments, the receptacle member includes a battery disposed therein. The battery is coupled to at least one of the electrical contacts of the receptacle member and is configured to supply power to the camera head when the camera head and the receptacle member are disposed in electrical communication with one another.

In embodiments, the camera head includes an optical lens and an image sensor. The optical lens is configured to project an image onto the image sensor. The image sensor is configured to convert the image into a signal and to transmit the signal to the receptacle member.

In embodiments, the receptacle member is configured to couple to a display device and to transmit the signal from the image sensor to the display device for displaying the signal as a video image.

In embodiments, the camera head includes at least one illumination source.

A method of providing visualization within an internal surgical site is also provided in accordance with the present disclosure. The method includes providing a surgical camera assembly including a camera member and a receptacle member, e.g., a surgical camera assembly similar to any of the embodiments above. The method further includes inserting the camera member into an internal surgical site, urging the shaft of the camera member through tissue such that the at least one electrical contact of the shaft is disposed on an external side of tissue while the camera head remains disposed on an interior side of tissue, and engaging the receptacle member to the shaft on the external side of tissue such that the at least one electrical contact of the shaft is electrically coupled to the at least one electrical contact of the receptacle member.

In embodiments, the method further includes transmitting at least one of power, control, and image signals between the camera head and the receptacle member.

In embodiments, the method further includes coupling the receptacle member to a display device.

In embodiments, the method further includes receiving an image of the internal surgical site with the camera head, transmitting a signal representing the image from the camera head to the receptacle member, transmitting the signal from the receptacle member to the display device, and displaying a video image corresponding to the electrical signal on the display device.

In embodiments, the method further includes processing the signal received from the camera head before transmitting the signal to the display device.

In embodiments, the method further includes illuminating the internal surgical site with the camera head.

BRIEF DESCRIPTION OF THE DRAWINGS

Various embodiments of the present disclosure are described herein with reference to the drawings wherein.

DETAILED DESCRIPTION

Embodiments of the present disclosure are described in detail with reference to the drawing figures wherein like reference numerals identify similar or identical elements. As used herein, the term "distal" refers to the portion that is being described which is farther from a user, while the term "proximal" refers to the portion that is being described which is closer to a user.

Figure 1:
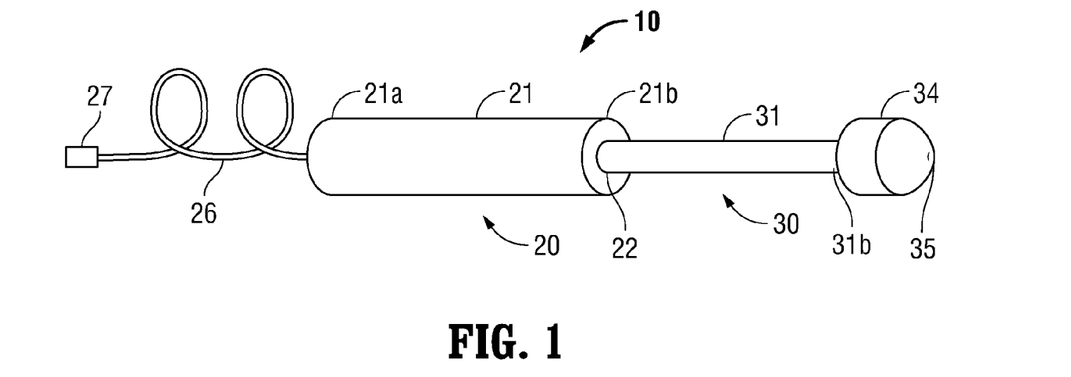
FIG. 1 is a side, perspective view of a surgical camera assembly provided in accordance with the present disclosure.
Figure 2A:
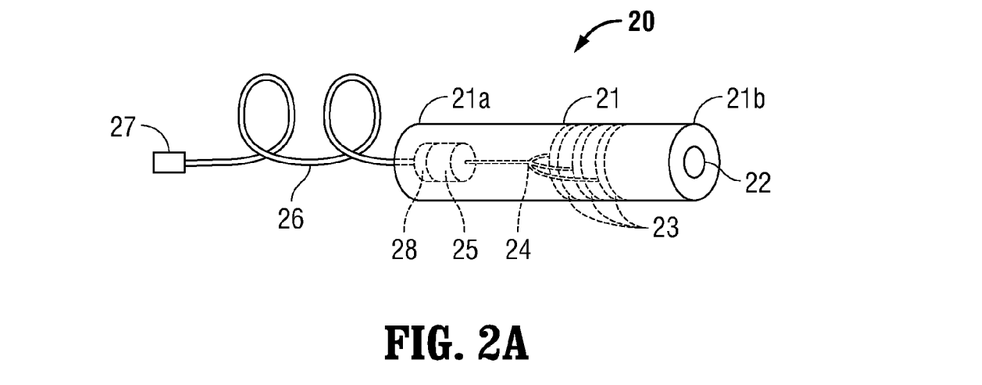
FIG. 2A is a side, perspective view of a receptacle member of the surgical camera assembly of FIG. 1.
Figure 2B:
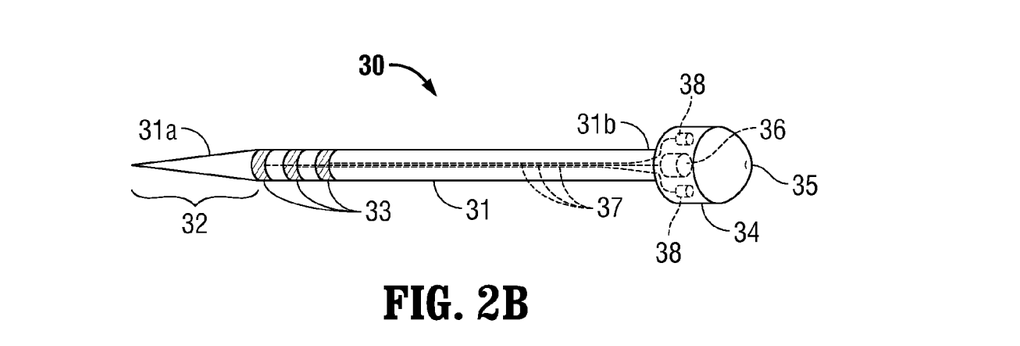
FIG. 2B is a side view of a camera member of the surgical camera assembly of FIG. 1.

Referring now to FIGS. 1-2B, a surgical camera assembly provided in accordance with the present disclosure is shown generally identified by reference numeral 10. Surgical camera assembly 10 generally includes a receptacle member 20 (FIG. 2A) and a camera member 30 (FIG. 2B). As will be described in greater detail below, receptacle member 20 and camera member 30 are configured to both mechanically engage and electrically couple to one another to facilitate mounting of surgical camera assembly 10 within tissue and transmitting power, image, and/or control signals therebetween.

With reference to FIG. 1 and FIG. 2A, receptacle member defines a generally cylindrical body 21 (although other configurations are also contemplated) including a proximal end 21a and a distal end 21b. A receiving port 22 is defined within cylindrical body 21 towards distal end 21b thereof and is configured to receive a portion of camera member 30 (FIG. 2B) to facilitate mechanical engagement and electrical coupling therebetween. Receiving port 22 includes a plurality of electrical contacts, e.g., ring contacts 23 (although other suitable contacts are also contemplated), disposed on the interior surface of cylindrical body 21 that defines receiving port 22. One or more wires 24 is coupled to contacts 23 for coupling contacts 23 to control circuitry 25 disposed within cylindrical body 21. As will be described below, control circuitry 21 is configured to process, modulate, and/or synthesize the signal(s) received from image sensor 36 (FIG. 2B) of camera member 30 and to output a video signal for display on a video monitor 200 (FIG. 5A), visualization goggles 300 (FIG. 5B), or other suitable display device. Control circuitry 25 may output the video signal via a cable 26 which extends proximally from cylindrical body 21 and culminates in a plug 27 to facilitate the coupling of receptacle member 20 to the desired display device. Alternatively, control circuitry 25 may be configured to wirelessly transmit the video signal to a wireless receiver associated with the desired display device. Once example of a wirelessly-configured surgical camera is disclosed in U.S. patent application Ser. No. 13/025,636, the entire contents of which are hereby incorporated by reference herein.

Continuing with reference to FIGS. 1 and 2A, receptacle member 20 may be battery-powered, e.g., receptacle member 20 may include a battery 28 disposed within body 21 thereof for powering receptacle member 20 and camera member 30 (FIG. 2B), or may be configured to connect to a power source via cable 26 or other wired power connection. As can be appreciated, in embodiments where receptacle member 20 is battery-powered, and where control circuitry 25 is configured to wirelessly transmit the video signal(s) to a display, receptacle member 20 need not require any external cables or wires, rendering receptacle member 20 fully wireless. U.S. patent application Ser. No. 13/025,636, previously incorporated by reference herein, discloses a similar configuration suitable for use in conjunction with receptacle member 20.

With reference to FIGS. 1 and 2B, camera member 30 includes a shaft 31 and a camera head 34. Shaft 31 defines a generally cylindrical configuration having a proximal end 31a and a distal end 31b. Camera head 34 is disposed at distal end 31b of shaft 31, while proximal end 31a of shaft 31 defines a pointed or needle-shaped portion 32 (although other configurations are also contemplated). Needle-shaped portion 32 of proximal end 31a of shaft 31 facilitates penetration and advancement of shaft 31 through tissue while minimizing trauma and collateral damage. Proximal end 31a of shaft 31 is configured to be at least partially received within receiving port 22 of receptacle member 20 (FIG. 2A) to mechanically engage camera member 30 and receptacle member 30 (FIG. 2A) to one another. More specifically, shaft 31 may be configured for friction-fit engagement within receiving port 22 (FIG. 2A), or may be configured for releasable mechanical engagement within receiving port 22 (FIG. 2A) in any other suitable fashion, e.g., via threaded coupling, latching, pin-aperture engagement, etc. Shaft 31 further includes a plurality of electrical contacts, e.g., ring contacts 33, disposed about the outer periphery thereof. Contacts 33 are configured to electrically interface with contacts 23 of receptacle member 20 (FIG. 2A) to establish electrical communication therebetween upon mechanical engagement of camera member 30 and receptacle member 20 (FIG. 2A) to one another, e.g., upon insertion of proximal end 31a of shaft 31 into receiving port 22 of body 21 (FIG. 2A).

Continuing with reference to FIGS. 1 and 2B, camera head 34 is disposed at distal end 31b of shaft 31. Although described herein as including imaging components for providing a video image of an internal surgical site, it is envisioned that camera head 34 be alternatively be configured as an illumination source, other imaging or mapping source, or any other suitable surgical tool configured to be mounted on an interior surface of tissue while also being electrically coupled to instrumentation or devices disposed exteriorly of the tissue. With respect to camera head 34 functioning as a video imaging device, camera head 34 includes one or more optical lenses 35 configured to project an optical image of the field of view onto an image sensor 36. Image sensor 36 is positioned to receive the optical image projected thereon by lens 35 and is configured to convert the optical image into an electrical signal. Image sensor 36 may be a CCD image sensor, CMOS image sensor, or any other suitable image sensor. Image sensor 36 is electrically coupled to one or more wires 37 that extend from image sensor 36 proximally though shaft 31, ultimately coupling to contacts 33. As such, the electrical signals representing the optical image can be transmitted from image sensor 36, across contacts 33 and 23 (FIG. 2A), to control circuitry 25 of receptacle member 20 (FIG. 2A) for transmission to a display device. Likewise, power and control signals may be transmitted from receptacle member 20 (FIG. 2A) to camera head 34 via contacts 23 (FIG. 2A) and 33, and the one or more wires 37. Camera head 34 may further include one or more illumination sources 38, e.g., LED's or other suitable light sources, configured to illuminate the field of view of lens 35 so as to facilitate visualization of the field of view. Illumination sources 38 may be powered and/or controlled similarly as described above with respect to image sensor 36. Although one configuration of video imaging components suitable for use with camera member 30 is described above, it is envisioned that camera member 30 may be configured in any other suitable fashion to facilitate video imaging of an internal surgical site.

Figure 3A:
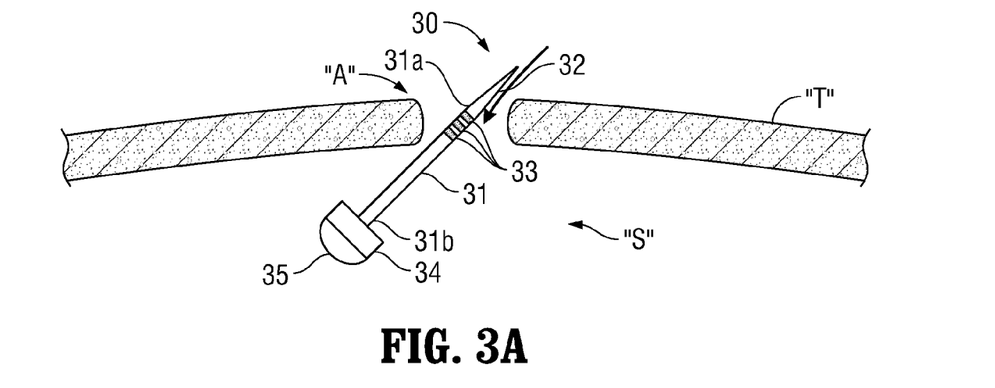
FIG. 3A is a cross-sectional view of an internal surgical site showing the camera member of FIG. 2B during insertion through an access opening in tissue.
Figure 3B:
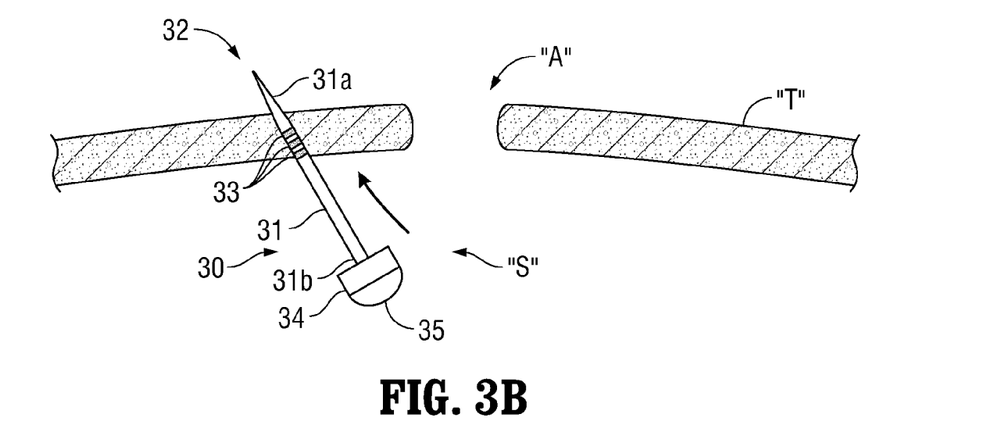
FIG. 3B is a cross-sectional view of the internal surgical site showing the camera member of FIG. 2B puncturing tissue for mounting the camera member within tissue after insertion of the camera member through the access opening.
Figure 3C:
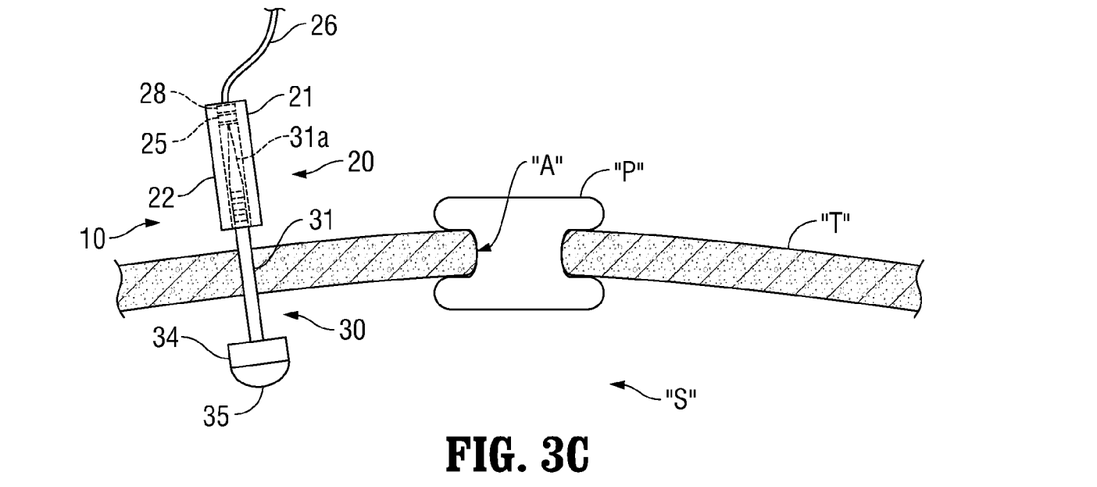
FIG. 3C is a cross-sectional view of the internal surgical site showing the surgical camera assembly of FIG. 1 mounted within tissue, and an access portal disposed within the access opening.

Turning now to FIGS. 3A-3C, in conjunction with FIGS. 1-2B, the insertion and mounting of surgical camera assembly 10 for use during a minimally-invasive surgical procedure is described. Initially, as shown in FIG. 3A, an access opening "A" is made through tissue "T" to provide access to the internal surgical site "S." Alternatively, a natural body orifice may be used as the access opening "A." Next, camera member 30 of surgical camera assembly 10 is inserted through the access opening "A" lead by camera head 34 so as to avoid accidental contact of needle-shaped portion 32 of proximal end 31a of shaft 31 with tissue "T." Alternatively, an access portal "P" may be positioned within the access opening "A" prior to insertion of camera member 30, such that camera member 30 may be inserted through the access portal "P" and into the internal surgical site "S." Whether camera member 30 is inserted directly through the access opening "A" or through the access portal "P" positioned within access opening "A" may depend on the user's preference, spatial considerations, or other factors.

As shown in FIG. 3B, once camera member 30 has been positioned within the internal surgical site "S," camera member 30 is oriented such that camera head 34 faces in a generally inward or distal direction, while needle-shaped portion 32 of proximal end 31a of shaft 31 faces in a generally outward or proximal direction. More specifically, camera head 34 is oriented so as to generally face the area to be visualized, e.g., such that the field of view of lens 35 covers the desired area to be viewed. With camera member 30 in position as desired, camera member 30, lead by needle-shaped portion 32, is urged proximally into contact with and, ultimately, penetrated through tissue "T." Shaft 31 is advanced proximally through tissue "T" sufficiently so as to expose contacts 33 on the external, or proximal side of tissue "T," while camera head 34 remains internally disposed within the internal surgical site "S," e.g., on a distal side of tissue "T."

As shown in FIG. 3C, with shaft 31 extending proximally from tissue "T" such that contacts 33 are exposed on the external or proximal side of tissue "T," receptacle member 20 may be engaged to shaft 31, e.g., proximal end 31a of shaft 31 of camera member 30 may be inserted into receiving port 22 of body 21 of receptacle member 20 to mechanically engage, e.g., via friction-fit, and electrically couple, e.g., via communication between contacts 33 and 23, camera member 30 and receptacle member 20 to one another. That is, with shaft 31 extending through tissue "T," the internally-disposed camera head 34 is mechanically and electrically coupled to the externally-disposed receptacle member 20. As can be appreciated, this configuration obviates the need for a relatively large incision that allows passage of camera head 34 and/or receptacle member 20 therethrough, the need for camera assembly 20 to occupy a portion of the access portal "P," and the need for various wires or other connections extending around and/or through the access portal "P" for interconnecting camera member 30 and receptacle member 20. If not done so already, once surgical camera assembly 10 is mounted within tissue "T," the access port "P" may be positioned within access opening "A" to facilitate the insertion of surgical instrumentation therethrough during the surgical procedure. The minimally-invasive surgical procedure to be performed may then proceed from there, facilitated by the visualization provided by surgical camera assembly 10.

As mentioned above, and with reference to FIGS. 1-2B and 3C, once mounted within tissue "T," surgical camera assembly 10 may be used to provide visualization, e.g., a video image or other suitable image, of the internal surgical site "S." More specifically, in use, surgical camera assembly 10 is activated, e.g., to supply power from battery 28 to receptacle member 20 and camera member 30. Once surgical camera assembly 10 is activated, illumination sources 38, if needed, are activated to illuminate the internal surgical site "S." With the internal surgical site "S" illuminated, optical lens 35 is better able to receive the optical image of the internal surgical site "S" or portion thereof and project the optical image of the field of view, e.g., the internal surgical site "S" or portion thereof, onto image sensor 36. Image sensor 36 converts the optical image into an electrical signal and communicates the electrical signal, via wires 37, contacts 33, 23, and wires 24 to control circuitry 25 of receptacle member 20. Control circuitry 25 may be configured to process the signal, e.g., to convert the signal from an analog signal to a digital signal, from a digital signal to an analog signal, or to modulate the signal. The processed signal (or unprocessed signal, in embodiments where processing is not required) is then output, e.g., via cable 26 and plug 27, or wirelessly, to a suitable display device for displaying the signal as a video image.

Figure 4:
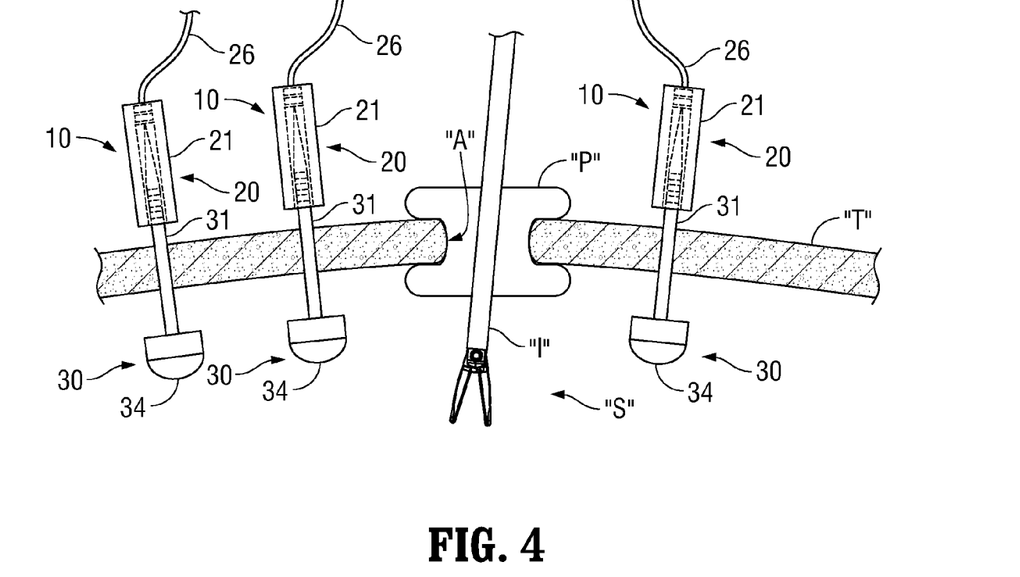
FIG. 4 is a cross-sectional view of an internal surgical site showing a surgical instrument inserted through an access portal disposed within an access opening in tissue, and a surgical camera system including a plurality of surgical camera assemblies mounted within tissue.

Turning now to FIG. 4, in conjunction with FIGS. 1-2B, a surgical camera system provided in accordance with the present disclosure is shown generally identified by reference numeral 100. Surgical camera system 100 is shown in use during a minimally-invasive surgical procedure and includes a plurality of surgical camera assemblies 10 mounted within tissue "T" at various locations. Although three surgical camera assemblies 10 are shown mounted at particular position within tissue "T," this configuration of surgical camera system 100 is for exemplary purposes only, as it is contemplated that the number and positioning of surgical camera assemblies 10 may be varied to achieve any suitable configuration depending on the procedure to be performed, the views needed, etc.

With continued reference to FIG. 4, in conjunction with FIGS. 1-2B, and as mentioned above, surgical camera system 100 is shown configured for visualizing an internal surgical site "S." More specifically, surgical cameral assemblies 10 of surgical camera system 100 are positioned about an access portal "P" including surgical instrumentation "I" inserted therethrough for performing a surgical procedure within the internal surgical site "S." Independently, each of the surgical camera assemblies 10 is configured and operates similarly as described above. However, providing multiple surgical camera assemblies 10 that cooperate to work in a system 100 allows panoramic, three-dimensional, multi-angle, or multi-camera visualization of the internal surgical site "S." That is, cables 26 of surgical camera assemblies 10 may be coupled to one another and/or a single display for displaying, for example, a panoramic or three-dimensional video image of the internal surgical site "S." Alternatively, cables 26 of surgical camera assemblies 10 may be coupled to separate displays (or a single display capable of displaying multiple video images), each of which is configured to display the video image of the surgical site from one of the surgical camera assemblies 10. Further, the illumination sources 38 of each surgical camera assembly 38 may be configured to illuminate the surgical site "S" with different wavelengths of light, thus providing for various different displays (or a single integrated display) including various different visual effects that facilitate the viewing of certain tissue structures, fluids, or instrumentation within the internal surgical site "S."

Figure 5A:
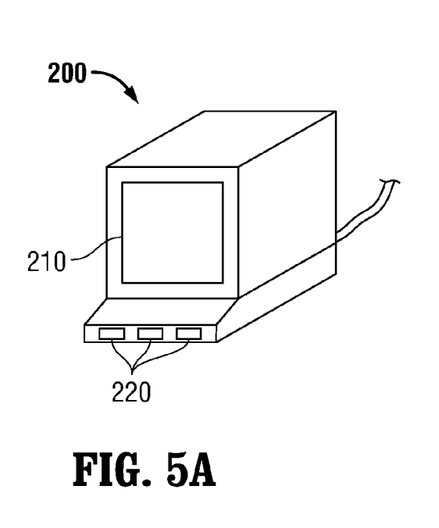
FIG. 5A is a perspective view of a video monitor configured for use in accordance with the present disclosure.
Figure 5B:
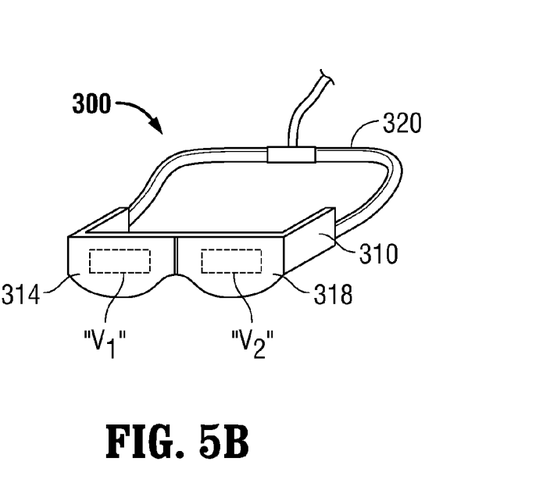
FIG. 5B is a perspective view of a pair of visualization goggles configured for use in accordance with the present disclosure.

With additional reference to FIGS. 5A and 5B, the display configured to receive the processed signal from one or more of the surgical camera assemblies 10 may be a video monitor 200, a pair of visualization goggles 300, or any other suitable display. Video monitor 200 includes a display screen 210 for displaying a video image of the internal surgical site "S" and one or more inputs 220 for receiving the plug 27 (FIG. 2A) of one or more surgical camera assemblies 10. Video monitor 200 is configured to convert the signal received from surgical camera assembly(s) 10 into a standard video image, three-dimensional video image, or panoramic video image, depending on a particular purpose and/or the particular settings selected by the user. Visualization goggles 300 are configured to be worn by the user and generally include a headset 310, a support strap 320 configured to secure headset 310 on a user's head, and one or more one or more inputs (not shown) for receiving the plug 27 (FIG. 2A) of one or more surgical camera assemblies 10. Headset 310 is positionable on the user's face and includes left and right lenses 314, 318, respectively, at least a portion of each of which is transparent so as not to substantially hinder the user's view when wearing visualization goggles 300. Headset 310 is configured to receive the electrical signals from surgical camera assemblies 10 and to convert the signals into a standard video image, three-dimensional video image, or panoramic video image, depending on a particular purpose and/or the particular settings selected by the user. Visualization goggles 300 are particularly suited for displaying three-dimensional and panoramic video images due to the ability to provide different video images for viewing by each of the user's eyes such that, when viewed together, the three-dimensional or panoramic video image is formed. Further, as an alternative to directly coupling visualization goggles 300 to surgical camera assembly(s) 10, goggles 300 may be coupled to video monitor 200 (or other suitable intermediate device) for relaying the video image to goggles 300 for displaying the video image to the user.

Referring to FIGS. 4 and 5A in particular, when a single surgical camera assembly 10 is coupled to video monitor 200, the signals from the control circuitry 25 of the receptacle member 20 (FIG. 2A) thereof are converted into a video image for display on display screen 210. With respect to multiple surgical camera assemblies 10 coupled to video monitor 200, the signals may be electronically synthesized to produce a panoramic or three-dimensional video image for display on display screen 210.

Referring to FIGS. 4 and 5B in particular, when used with visualization goggles 300, the signals of the multiple surgical camera assemblies 10 are electronically synthesized such that video images "V1" and "V2" are displayed on lenses 314, 318, respectively, of visualization goggles 300. Accordingly, with video images "V1" and "V2" displayed to the user directly in front of each of the user's eyes, a panoramic or three-dimensional video image of the internal surgical site "S" is seen by the user. With respect to a single surgical camera assembly 10, the video image thereof may be displayed on either of lenses 314, 318 so as to allow the user to view the internal surgical site "S" without having to look to a monitor.

Figure 6:
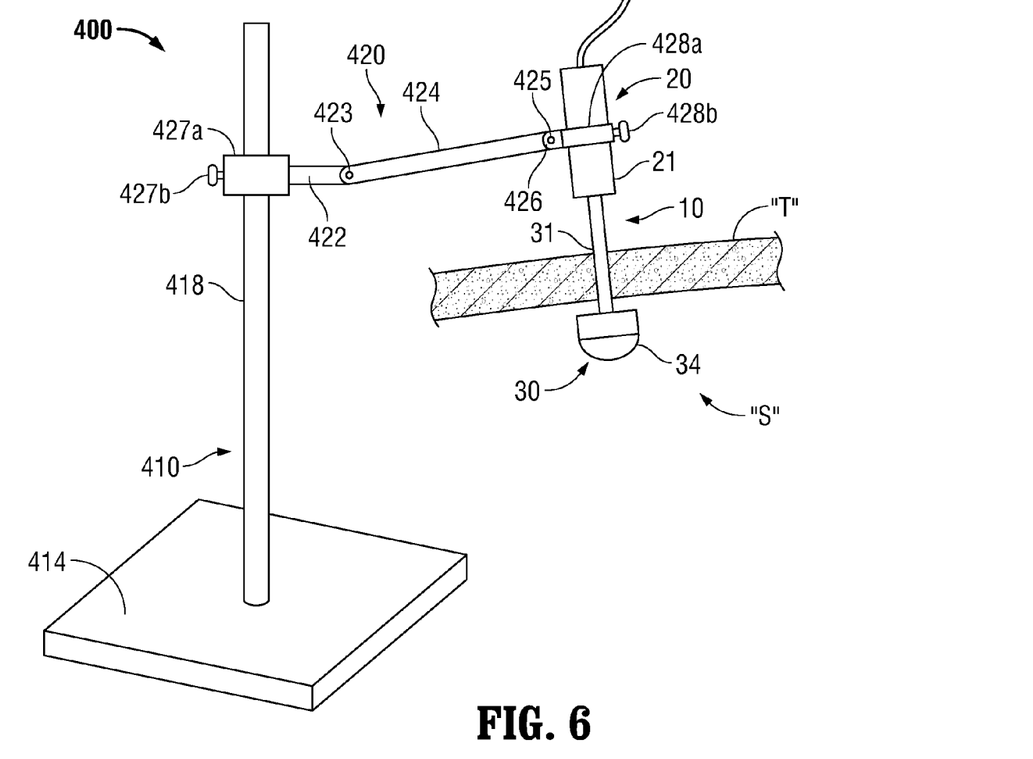
FIG. 6 is a perspective view of a surgical camera assembly mounted within tissue and coupled to an external support assembly provided in accordance with the present disclosure.

Referring now to FIG. 6, an external support assembly configured to support one or more surgical camera assemblies 10 to maintain positioning of the one or more surgical camera assemblies 10 during use is shown generally identified by reference numeral 400. External support assembly 400 generally includes a support base 410 and one or more support arms 420. Although only one support arm 420 is shown, it is envisioned that a plurality of similarly configured support arms 420 be provided for supporting a plurality of surgical camera assemblies 10 in a desired configuration. As can be appreciated, external support assembly 400 may thus be used to orient and position the various surgical camera assemblies 10 of a surgical camera system, e.g., surgical camera system 100 (FIG. 4).

With continued reference to FIG. 6, support base 410 includes a base member 414 that is configured to stabilize and support external support assembly 400, and one or more support posts 418 that extend vertically from base member 414. Each of the support arms 420 is slidably mounted on support post 418 at one end thereof and releasably engages one of the surgical camera assemblies 10 at the other end. Each support arm 420 may includes a plurality of segments 422, 424, 426 interconnected by hinges or joints 423, 425 to facilitate manipulating the support arm 420 to a desired configuration for retaining a surgical camera assembly 10 in a desired position. Each support arm 420 further includes first and second cuffs 427a, 427b. First cuff 427a is coupled to first segment 422 and is slidably disposed about support post 418. A lock fastener 427b for securing first cuff 427a and, thus, support arm 420, at any vertical position along support post 418 is also provided. Second segment 424 of support arm 420 is interconnected to first and third segments 422, 426 via joints 423, 425, respectively. Second cuff 428a is disposed about body 21 of the receptacle member 20 of surgical camera assembly 10 and likewise includes a lock fastener 428b for releasably securing second cuff 428a and, thus, support arm 420, to surgical camera assembly 10.

Figure 7A:
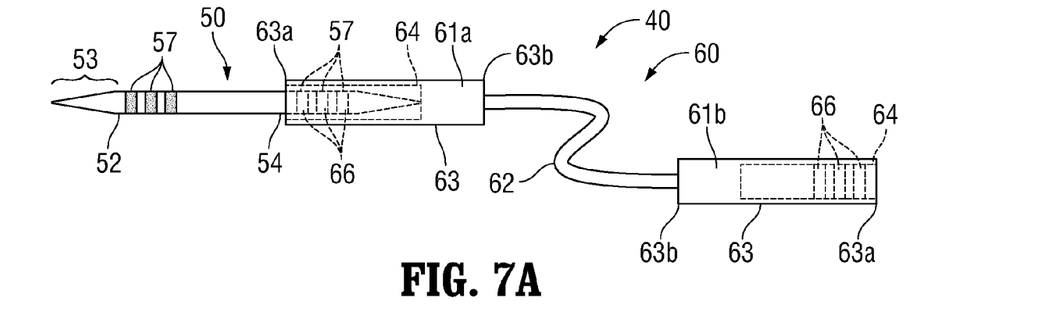
FIG. 7A is a side view of a connection assembly configured for use with the surgical camera assembly of FIG. 1 and provided in accordance with the present disclosure.
Figure 7B:
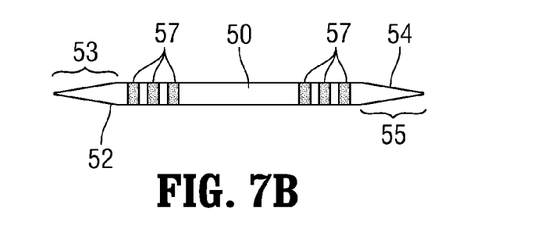
FIG. 7B is a side view of a shaft connector of the connection assembly of FIG. 7A.
Figure 7C:
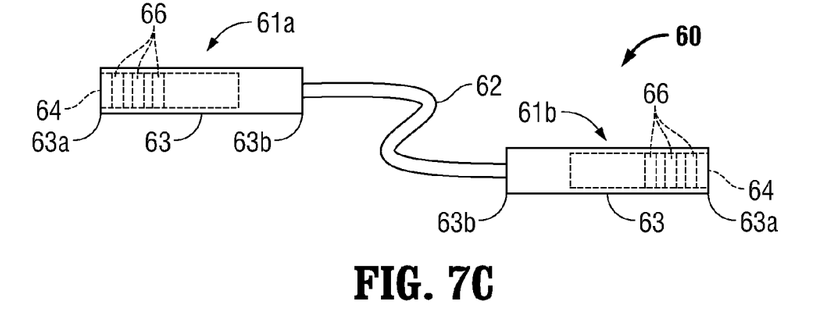
FIG. 7C is a side view of a receptacle connector of the connection assembly of FIG. 7A.

Turning now to FIGS. 7A-7D, in conjunction with FIGS. 1-2B, various different connecting components may be provided for use with surgical camera assembly 10 to further facilitate the positioning of surgical camera assembly 10 as desired to visualize the internal surgical site "S" or portion thereof. For example, FIGS. 7A-7C show a connection assembly 40 provided in accordance with the present disclosure that includes a shaft connector 50 (FIG. 7B) and a receptacle connector 60 (FIG. 7C). However, although exemplary connection assembly 40 is shown including one shaft connector 50 (FIG. 7B) and one receptacle connector 60 (FIG. 7C), it is contemplated that multiple shaft connectors 50 (FIG. 7B) and/or multiple receptacle connectors 60 (FIG. 7C) be provided to form a customized connection assembly for use with one or more receptacle members 20 (FIG. 2A), one or more camera members 30 (FIG. 2B), and/or one or more other connection assemblies, e.g., another connection assembly 40 and/or a different connection assembly 70 (FIG. 7D), to achieve a desired configuration.

Figure 7D:
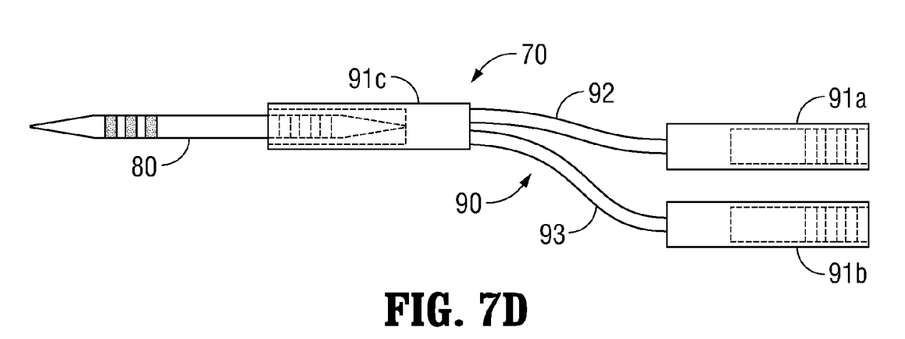
FIG. 7D is a side view of another connection assembly provided in accordance with the present disclosure.

With reference to FIGS. 7A-7C, and in particular to FIG. 7B, shaft connector 50 is configured to interconnect, e.g., mechanically and electrically couple, a pair of receptacles to one another, e.g., receptacle member 20 of surgical camera assembly 10 (FIGS. 1 and 2A) and a receptacle member 61a, 61b of connection assembly 40 (FIG. 7C) or the receptacle members 61a-61b, 91a-91c of different connection assemblies 40, 70 (FIGS. 7C and 7D, respectively). Shaft connector 50 includes first and second ends 52, 54, respectively, one or both of which defines a needle-shaped portion 53, 55, respectively, although other configurations are also contemplated. As described above, needle-shaped portions 53, 55 facilitate penetration and advancement of shaft connector 50 through tissue while minimizing trauma and collateral damage. Each end 52, 54 of shaft connector 50 may be configured for friction-fit engagement within a port, e.g., receiving port 22 of surgical camera assembly 10 (FIG. 2A) or receiving port 64 of receptacle connector 60, or may be configured for releasable mechanical engagement with a port in any other suitable fashion, e.g., via threaded coupling, latching, pin-aperture engagement, etc. Shaft connector 50 further includes a plurality of electrical contacts, e.g., ring contacts 57, disposed about the outer periphery thereof towards each end 52, 54 thereof. Contacts 57 are configured to electrically interface with the contacts disposed within the port, e.g., contacts 23 of receptacle member 20 (FIG. 2A) or contacts 66 of receptacle port 64 of receptacle member 61a to establish electrical communication therebetween. As can be appreciated, shaft connector 50 provides the ability to both electrically and mechanically connect otherwise incompatible components, e.g., two receptacles.

With reference to FIGS. 7A-7C, and in particular to FIG. 7C, receptacle connector 60 includes a pair of receptacle members 61a, 61b interconnected by a cable 62. Each receptacle member 61a, 61b is similar to receptacle member 20 of surgical camera assembly 10 (FIGS. 1-2B) and includes a body 63 defining first and second ends 63a, 63b, respectively. A receiving port 64 is defined within body 63 towards one of the ends, e.g., end 63a, thereof and is configured to receive shaft 31 of camera member 30 (FIG. 2B) and/or shaft connector 50 to facilitate mechanical engagement and electrical coupling therebetween. The receptacle members 61a, 61b are coupled to one another at the other ends 63b thereof via cable 62. Receiving port 64 further includes a plurality of electrical contacts, e.g., ring contacts 66 (although other suitable contacts are also contemplated), disposed on the interior surface of body 63 that defines receiving port 64. One or more wires (not shown) couples contacts 66 to cable 62, which extends between receptacle members 61a, 61b, such that receptacle members 61a, 61b are electrically coupled to one another. One or both receptacle members 61a, 61b may include control circuitry, a battery, or other electronics disposed therein, or may simply be configured as a connection component for establishing electrical communication between other active components, e.g., a camera member 30 and receptacle member 20 of a surgical camera assembly 10 (FIGS. 1-2B). As can be appreciated, receptacle connector 60 provides the ability to both electrically and mechanically connect otherwise incompatible components, e.g., two shafts.

Referring now to FIG. 7D, another exemplary connection assembly 70 provided in accordance with the present disclosure is shown including a shaft connector 80 and a two-to-one receptacle connector 90. Shaft connector 80 may be configured similarly to shaft connector 50 of connection assembly 40 (FIGS. 7A-7C), described above. Two-to-one receptacle connector 90 is similar to receptacle connector 60 of connection assembly 40 (FIGS. 7A-7C), except that two-to-one receptacle connector 90 includes a single receptacle member 91c coupled to a pair of receptacle members 91a, 91b via first and second cables 92, 93, respectively. As can be appreciated, connection assembly 70 permits the coupling, for example, of two camera members 30 (FIGS. 1-2B) to a single receptacle member 20 (FIGS. 1-2B), thus providing for the use of two surgical cameras while only requiring that a single penetrate tissue. Connection assembly 70 may further be configured for use with one or more similar connection assemblies 70, one or more shaft connectors 50 (FIG. 7B), one or more receptacle connectors 60 (FIG. 7C), and/or one or more surgical camera assemblies 10 (FIGS. 1-2B).

Figure 7E:
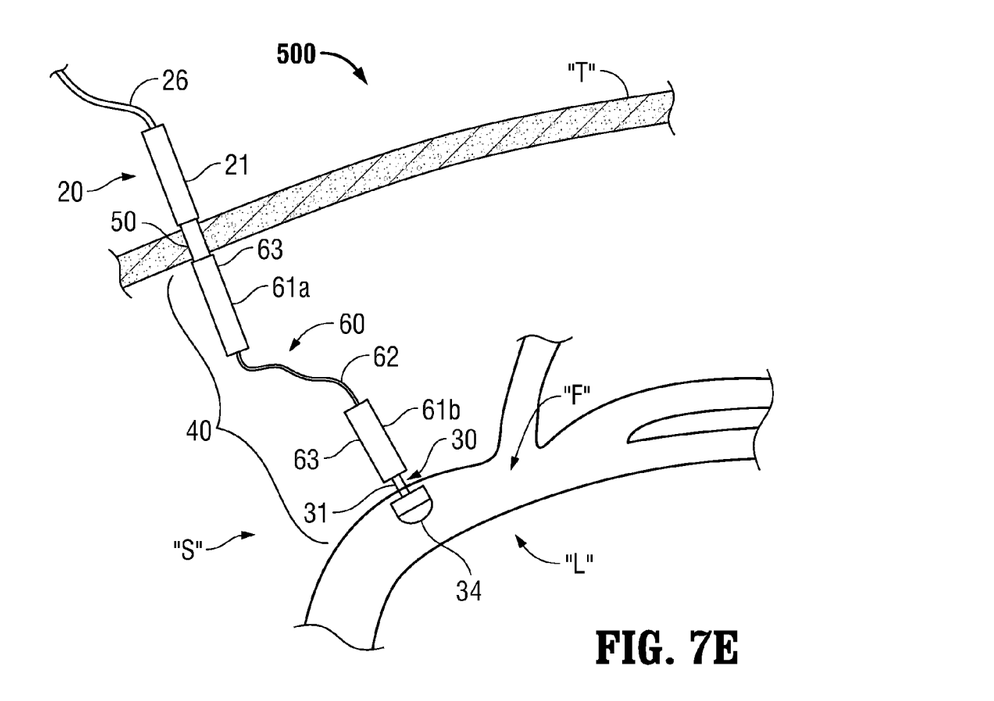
FIG. 7E is a cross-sectional view of an internal surgical site showing the connection assembly of FIG. 7A used in conjunction with the surgical camera assembly of FIG. 1 for visualizing the interior of an internal tissue structure disposed within the internal surgical site.

Turning now to FIG. 7E, in conjunction with FIGS. 1-2B and 7A-7C, a surgical camera system including a surgical camera assembly 10 (FIGS. 1-2B) and a connection assembly 40 (FIGS. 7A-7C) in cooperative use for visualizing the interior of an internal tissue structure, e.g., a body lumen "L," is shown generally identified by reference numeral 500. Surgical camera system 500 is shown by way of example only, as it is contemplated that any or all of the various other surgical camera and connection components described above may be used in cooperation with one another to provide a surgical camera system for visualizing any internal surgical site "S" or portion thereof.

With continued reference to FIG. 7E, in conjunction with FIGS. 1-2B and 7A-7C, in order to install surgical camera system 500, camera member 30 is inserted into the interior "F" of body lumen "L." Once positioned within body lumen "L," shaft 31 of camera member 30 is urged proximally into contact with and, ultimately, penetrated through the wall of body lumen "L" sufficiently so as to expose contacts 33 (FIG. 2B) on the external side of body lumen "L," while camera head 34 remains disposed within body lumen "L."

Next, connection assembly 40 is assembled to achieve the configuration shown in FIG. 7A, wherein second end 54 of shaft connector 50 is mechanically engaged and electrically coupled within receiving port 64 of first receptacle member 61a of receptacle connector 60, and is inserted into the internal surgical site "S." Although positioned within the internal surgical site "S," connection assembly 40 remains externally disposed relative to body lumen "L." That is, connection assembly 40 need not be disposed within body lumen "L" since, similarly as described above, with shaft 31 of camera member 30 extending proximally through the wall of body lumen "L," the second receptacle member 61b of receptacle connector 60 may be electrically coupled and mechanically engaged to shaft 31 via inserting shaft 31 into receiving port 64 of second receptacle member 61b.

Referring still to FIG. 7E in conjunction with FIGS. 1-2B and 7A-7C, either before or after the coupling of second receptacle member 61b to shaft 31, first end 52 of shaft connector 50, which defines needle-shaped portion 53, is advanced proximally to penetrate through tissue "T," such that first end 52 of shaft connector 50 extends proximally or externally from tissue "T." Thus, at this point: camera head 34 is disposed within the interior "F" of body lumen "L;" shaft 31 extends from camera head 34 through the wall of body lumen "L;" second receptacle member 61b of receptacle connector 60 is coupled to shaft 31 within the internal surgical site "S" but externally of the body lumen "L;" first receptacle member 61a of receptacle connector 60, which is coupled to the second receptacle member 61b via cable 62, is coupled to second end 54 of shaft connector 50; and shaft connector 50 extends proximally through tissue "T" such that first end 52 of shaft connector 50 is disposed externally of tissue "T." Put more generally, due to the above-described connections, at this point, camera head 34 is electrically coupled to contacts 57 (FIG. 7B) disposed at first end 52 of shaft connector 50, which extends externally from tissue "T."

In order to complete installation of surgical camera system 500, receptacle member 20 is mechanically engaged and electrically coupled to first end 52 of shaft connector 50 via inserting first end 52 of shaft connector 50 into receiving port 22 of receptacle member 20, similarly as described above. Cable 26 of receptacle member 20 may then be coupled to a display device, e.g., monitor 200 (FIG. 5A) or visualization goggles 300 (FIG. 5B). The use and operation of surgical camera system 500 for visualizing the interior "F" of body lumen "L" is otherwise similar to that described above with respect to surgical camera assembly 10 (FIGS. 1-3C) except that the power, control, and image signals are transmitted between camera head 34 and receptacle member 34 (and ultimately to a suitable display device) via connection assembly 40, rather than directly between contacts 33 of camera member 30 and contacts 23 of receptacle member 20.

Figure 8A:
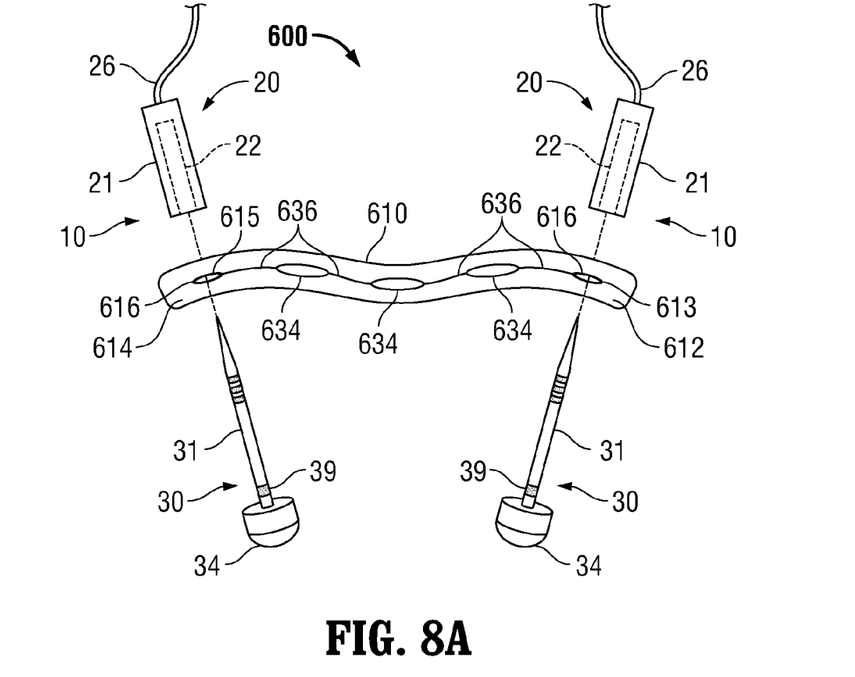
FIG. 8A is a perspective view of a surgical camera array assembly provided in accordance with the present disclosure.
Figure 8B:
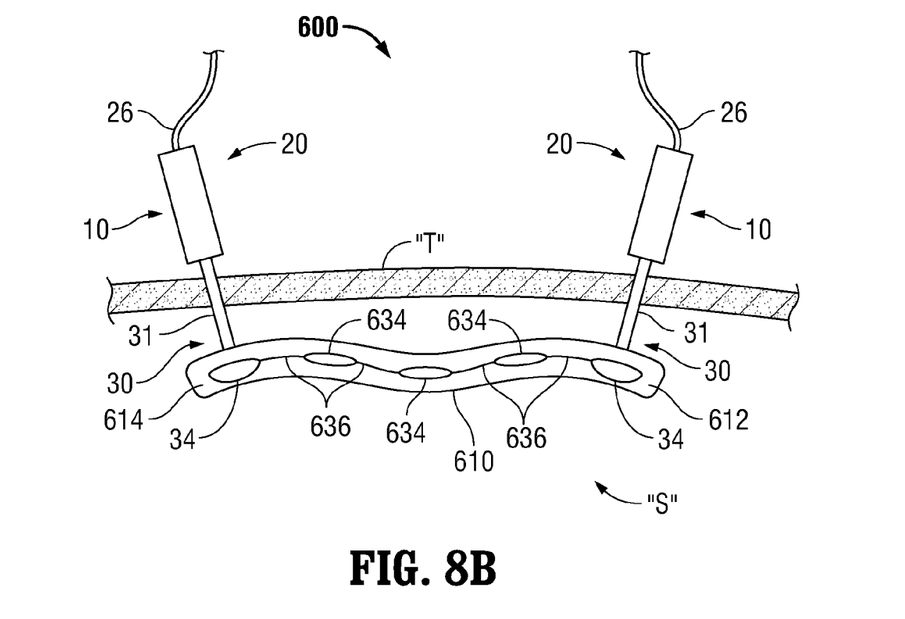
FIG. 8B is a cross-sectional view of an internal surgical site showing the surgical camera array assembly of FIG. 8A mounted within tissue for visualizing the internal surgical site.

Turning now to FIGS. 8A-8B, a surgical camera array assembly provided in accordance with the present disclosure and configured for use independently of or in conjunction with any of the embodiments of surgical camera assemblies, connection assemblies, or surgical camera systems described above is shown generally identified by reference numeral 600. Surgical camera array assembly 600 includes a flexible substrate 610 defining a generally rectangular configuration (although other configurations are contemplated) and having first and second ends 612, 614. Flexible substrate 610 further includes an aperture 613, 615 defined therethrough towards each end 612, 614, respectively, thereof. A contact ring 616 surrounds each aperture 613, 615. One or more camera heads 634 (similar to camera head 34 (FIG. 2B), described above) is disposed on and positioned along flexible substrate 610 between apertures 613, 615. Alternatively or additionally, illumination sources, other imaging or mapping components, or other surgical tools may be disposed along flexible substrate 610 similarly as camera heads 634. Camera heads 634 are electrically coupled to one another and/or contact rings 616 of apertures 613, 615 via wires 636 such that power, control, and/or imaging signals may be transmitted therebetween. Camera heads 634 may further be configured for releasably engagement with flexible substrate 610 such that a desired number and/or configuration of camera heads 634 (or other components) may be installed on flexible substrate 610 as desired.

With continued reference to FIGS. 8A-8B, apertures 613, 615 of flexible substrate 610 are each configured to receive a shaft 31 of a camera member 30 of a surgical camera assembly 10 (or similar components of a connection assembly 40 (FIGS. 7A-7C)). Shafts 31 each include an additional contact ring 39 that is configured to interface with the contact ring 616 of the respective aperture 613, 615 upon insertion of shaft 31 therethrough, thus establishing electrical communication between camera members 30 and camera heads 634 via wires 636, contact rings 616, and contact rings 39. The needle-shaped ends 32 of shafts 31 may then be mechanically engaged and electrically coupled to receptacle members 20 such that power, control, and/or image signals may be transmitted between receptacle members 20 and any or all of the camera heads 34, 634. As can be appreciated, this configuration of surgical camera array assembly 600 allows the use of a plurality of surgical cameras within the internal surgical site "S" without requiring the puncturing of tissue "T" for mounting each surgical camera.

Continuing with reference to FIGS. 8A-8B, in conjunction with FIGS. 1-2B, the insertion and mounting of surgical camera array assembly 600 for use during a minimally-invasive surgical procedure is described. Initially, flexible substrate 610, having camera heads 634 mounted thereon, is inserted into the internal surgical site "S;" camera members 30 of surgical camera assemblies 10 are inserted into the internal surgical site "S;" and shafts 31 of camera members 30 are inserted through apertures 613, 615 defined within flexible substrate 610 such that contact rings 39 and contact rings 616 are electrically coupled to one another. The insertion of flexible substrate 610, the insertion of camera members 30, and the insertion of shafts 31 through apertures 613, 615 may be performed in any order. At this point, the relatively larger dimensions of camera heads 34 of camera members 30 as compared to apertures 613, 615 of flexible substrate 610 inhibits flexible substrate 610 from sliding distally off of shafts 31.

Next, camera members 30, having flexible substrate 610 disposed thereon, are urged proximally, lead by needle-shaped portions 32, into contact with and, ultimately, penetrated through tissue "T." Shafts 31 are advanced proximally through tissue "T" sufficiently so as to expose contacts 33 on the external side of tissue "T," while camera heads 34 and flexible substrate 610, including camera heads 636, remain disposed within the internal surgical site "S."

With shafts 31 extending proximally from tissue "T," receptacle members 20 may be engaged to shafts 31 via insertion of shafts 31 of camera members 30 into receiving ports 22 of bodies 21 of receptacle members 20 to mechanically engage, e.g., via friction-fit, and electrically couple, e.g., via communication between contacts 33 and 23, camera members 30 and receptacle members 20 to one another. In this assembled condition, surgical camera assemblies 10 are mounted within tissue "T" and flexible substrate 610 is retained via shafts 31, camera heads 34, and tissue "T." The minimally-invasive surgical procedure to be performed may then proceed, facilitated by the visualization provided by surgical camera array assembly 600. The use of surgical camera array assembly 600 for visualizing the internal surgical site "S" is similar to that described above, with any or all of the camera heads 34, 634 operating independently of one another or in cooperation with one another to provide standard, panoramic, three-dimensional, multi-angle, or multi-camera visualization of the internal surgical site From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical camera assembly, comprising:
   a shaft having opposed first and second ends, each end including a needle-shaped configuration to facilitate penetration through tissue and at least one electrical contact;
   a camera member including a camera head; and
   a receptacle member having first and second openings, the first opening configured to releasably receive the first end of the shaft and the second opening configured to releasably receive a portion of the camera member, the receptacle member including at least one electrical contact configured to electrically couple to the at least one electrical contact of the first end to establish electrical communication between the camera head and the shaft when the first end of the shaft is received within the first opening of the receptacle member and the portion of the camera member is received within the second opening of the receptacle member.

2. The surgical camera assembly according to claim 1, wherein the receptacle member defines a receiving port configured to receive one of the first or second ends of the shaft.

3. The surgical camera assembly according to claim 2, wherein at least one electrical contact of the shaft is disposed about an outer periphery of the shaft and wherein the at least one electrical contact of the receptacle member is disposed within the receiving port, such that electrical communication is established between the shaft and the receptacle member when the shaft is coupled to the receptacle member.

4. The surgical camera assembly according to claim 2, wherein the first and second ends of the shaft are configured for releasable friction-fit engagement within the receiving port of the receptacle member.

5. The surgical camera assembly according to claim 1, wherein the receptacle member includes control circuitry disposed therein, the control circuitry coupled to the at least one electrical contact of the receptacle member and configured to transmit control signals to the camera head when the camera head and the receptacle member are disposed in electrical communication with one another.

6. The surgical camera assembly according to claim 1, wherein the receptacle member includes a battery disposed therein, the battery coupled to the at least one electrical contact of the receptacle member and configured to supply power to the camera head when the camera head and the receptacle member are disposed in electrical communication with one another.

7. The surgical camera assembly according to claim 1, wherein the camera head includes an optical lens and an image sensor, the optical lens configured to project an image onto the image sensor, the image sensor configured to convert the image into a signal and to transmit the signal to the receptacle member.

8. The surgical camera assembly according to claim 7, wherein the receptacle member is configured to couple to a display device, the receptacle member configured to transmit the signal from the image sensor to the display device for displaying a video image corresponding to the signal.

9. The surgical camera assembly according to claim 1, wherein the camera head includes at least one illumination source.

10. A method of providing visualization within an internal surgical site, the method comprising:
    providing a surgical camera assembly including:
      a receptacle member having first and second openings and at least one electrical contact;
      a camera member having a camera head and a coupling portion, the coupling portion including a needle-shaped configuration to facilitate penetration through tissue and at least one electrical contact, the at least one electrical contact electrically coupled to the camera head, the coupling portion releasably attachable to the receptacle member;
      a shaft having opposed first and second ends, each end including a needle-shaped configuration to facilitate penetration through tissue and at least one electrical contact; and
    inserting the camera member into an internal surgical site;
    urging the coupling portion through tissue such that the at least one electrical contact of the coupling portion is disposed on an external side of tissue, while the camera head remains disposed on an interior side of tissue;
    engaging the first opening of the receptacle member to the coupling portion on the external side of tissue such that the at least one electrical contact of the coupling portion is electrically coupled to the at least one electrical contact of the receptacle member; and
    establishing electrical communication between the camera member and the shaft when the first end of the shaft is received within the second opening of the receptacle member and the coupling portion is received within the first opening of the receptacle member.

11. The method according to claim 10, further comprising transmitting at least one of power, control, and image signals between the camera head and the receptacle member.

12. The method according to claim 10, further comprising coupling the receptacle member to a display device.

13. The method according to claim 12, further comprising:
- receiving an image of the internal surgical site with the camera head;
- transmitting a signal representing the image from the camera head to the receptacle member;
- transmitting the signal from the receptacle member to the display device; and
- displaying a video image corresponding to the signal on the display device.

14. The method according to claim 13, further comprising processing the signal received from the camera head before transmitting the signal to the display device.

15. The method according to claim 13, further comprising illuminating the internal surgical site with the camera head.

\* \* \* \* \*